US012571011B2

(12) United States Patent
Ye et al.

(10) Patent No.: US 12,571,011 B2
(45) Date of Patent: Mar. 10, 2026

(54) VISCOUS POLYHYDROXYALKANOATE, PREPARATION THEREOF, AND USE THEREOF

(71) Applicant: SOUTH CHINA UNIVERSITY OF TECHNOLOGY, Guangdong (CN)

(72) Inventors: Jianwen Ye, Guangzhou (CN); Yina Lin, Guangzhou (CN); Xinying Xie, Guangzhou (CN)

(73) Assignee: SOUTH CHINA UNIVERSITY OF TECHNOLOGY, Guangdong (CN)

( * ) Notice: Subject to any disclaimer, the term of this patent is extended or adjusted under 35 U.S.C. 154(b) by 0 days.

(21) Appl. No.: 18/293,690

(22) PCT Filed: Nov. 28, 2023

(86) PCT No.: PCT/CN2023/134612
§ 371 (c)(1),
(2) Date: Jan. 30, 2024

(87) PCT Pub. No.: WO2024/088435
PCT Pub. Date: May 2, 2024

(65) Prior Publication Data
US 2025/0163479 A1 May 22, 2025

(30) Foreign Application Priority Data
Oct. 26, 2022 (CN) .......................... 202211318363.0

(51) Int. Cl.
| | |
|---|---|
| *C12P 7/625* | (2022.01) |
| *C12N 9/10* | (2006.01) |
| *C12N 15/70* | (2006.01) |
| *C12N 15/78* | (2006.01) |

(52) U.S. Cl.
CPC ............ *C12P 7/625* (2013.01); *C12N 9/1029* (2013.01); *C12N 15/70* (2013.01); *C12N 15/78* (2013.01)

(58) Field of Classification Search
CPC ....... C12P 7/625; C12N 9/1029; C12N 15/70; C12N 15/78
See application file for complete search history.

(56) References Cited

U.S. PATENT DOCUMENTS

| | | | |
|---|---|---|---|
| 4,867,155 A | 9/1989 | Isaacson | |
| 6,872,564 B1 | 3/2005 | Doi et al. | |
| 2009/0227893 A1 | 9/2009 | Coonahan et al. | |
| 2015/0105791 A1 | 4/2015 | Truckai | |

FOREIGN PATENT DOCUMENTS

| | | |
|---|---|---|
| AU | 771433 B2 | 7/2000 |
| AU | 2000024949 A1 | 7/2000 |
| CN | 101096651 A | 1/2008 |
| CN | 101270345 A | 9/2008 |
| CN | 101845414 A | 9/2010 |
| CN | 101919716 | 12/2010 |
| CN | 103361326 A | 10/2013 |
| CN | 103571894 A | 2/2014 |
| CN | 105603005 A | 5/2016 |
| CN | 107205733 | 9/2017 |
| CN | 109266597 A | 1/2019 |
| CN | 111235173 A | 6/2020 |
| CN | 111836589 | 10/2020 |
| CN | 113476111 | 10/2021 |
| CN | 113583922 A | 11/2021 |
| CN | 113684169 A | 11/2021 |
| CN | 216495408 | 5/2022 |
| CN | 114711838 | 7/2022 |
| CN | 115813454 | 3/2023 |
| EP | 0841036 | 5/1998 |
| EP | 0881293 A1 | 12/1998 |
| WO | WO 1990015143 A1 | 12/1990 |

OTHER PUBLICATIONS

Hofmann et al., GenBank accession No. TVT83278 disclosed Jul. 30, 2019.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Ng et al., Journal of Science and Bioengineering 122(5):550-557, 2016.*
Li et al., Advanced Materials 33, 2102766, pp. 1-14, 2021.*
PCT International Search Report and Written Opinion for corresponding PCT Application No. PCT/CN2023/134218, dated Mar. 4, 2024, 18 pages.
Li et al, "Tailor-Made Polyhydroxyalkanoates by Reconstructing Pseudomonas Entomophila", Advanced Materials, vol. 33, 2021, 14 pages.
Li et al, "Tailor-Made Polyhydroxyalkanoates by Reconstructing Pseudomonas Entomophila", Supporting Information, Advanced Materials, 34 pages (2021).
Li et al, "Engineering Pseudomonas entomophila for Synthesis of Copolymers with Defined Fractions of 3-Hydroxybutyrate and Medium-chain-length 3-Hydroxyalkanoates", Metabolic Engineering, 2018, 31 pages.
Grant Decision (with English translation) received in corresponding Application No. CN 202211318363.0 dated Nov. 23, 2023, 4 pages.

(Continued)

*Primary Examiner* — Delia M Ramirez
(74) *Attorney, Agent, or Firm* — Dority & Manning, PA

(57) ABSTRACT

The present application relates to the field of microbiological technology, and particularly relates to a viscous polyhydroxyalkanoate, and its preparation and use. The viscous polyhydroxyalkanoate can be produced by fermenting a *Pseudomonas* strain containing a mutant of PHA polymerase $PhaC_{61-3}$, and can be used for the preparation of biodegradable products.

10 Claims, 6 Drawing Sheets

Specification includes a Sequence Listing.

(56)        References Cited

OTHER PUBLICATIONS

Office Action (with English translation) received in corresponding
Application No. CN 202211318363.0, dated Aug. 18, 2023, 17
pages.

* cited by examiner

VISCOUS POLYHYDROXYALKANOATE, PREPARATION THEREOF, AND USE THEREOF

SEQUENCE LISTING

This application contains a Sequence Listing which has been submitted electronically in XML file format and is hereby incorporated by reference in its entirety. Said XML copy is named ACIP-204-PCT-US_Sequence Listing.xml and is 9,685 bytes in size.

CROSS-REFERENCE TO RELATED APPLICATIONS

This application is an U.S. national phase application under 35 U.S.C. § 371 based upon international patent application No. PCT/CN2023/134612 filed on Nov. 28, 2023, which itself claims priority to Chinese patent application No. 2022113183630, titled "VISCOUS POLYHY-DROXYALKANOATE, PREPARATION THEREOF, AND USE THEREOF", filed on Oct. 26, 2022. The contents of the above identified applications are hereby incorporated herein in their entireties by reference.

TECHNICAL FIELD

The present application relates to the field of microbiological technology, and particularly relates to a viscous polyhydroxyalkanoate, and its preparation and use.

BACKGROUND

Polyhydroxyalkanoates (PHAs) are polyesters intracellularly synthesized in a variety of microorganisms, and primarily found as storage materials for carbon sources and energy in organisms. PHAs possess physical and chemical properties similar to synthetic plastics, as well as superior features not found in synthetic plastics such as biodegradability, biocompatibility, optical activity, piezoelectricity, and gas barrier property. PHAs have broad application prospects in biodegradable packaging materials, tissue engineering materials, controlled-release materials, electrical materials, and medical materials.

There are methods for preparing conventional PHAs, such as those disclosed in CN114480317A, CN114480318A, etc. However, the varieties of conventional PHAs are limited, and viscous PHAs have not been reported.

The present application is filed in view of the above.

SUMMARY

Based on this, according to various embodiments of the present application, a viscous PHA and its preparation and use are provided. The technical solutions are as follows:

In a first aspect of the present application, a mutant of PHA polymerase $PhaC_{61-3}$ is provided. The mutant has the following amino acid mutation sites: E115T, A261E, R360S, and K457Q. The PHA polymerase $PhaC_{61-3}$ has an amino acid sequence as set forth in SEQ ID NO: 9.

In a second aspect of the present application, a nucleic acid fragment is provided. The nucleic acid fragment encodes the mutant.

In a third aspect of the present application, a recombinant vector is provided. The vector includes the nucleic acid fragment.

In a fourth aspect of the present application, a genetically engineered bacterium is provided. The bacterium is *Escherichia coli* containing the recombinant vector, or the bacterium is *Pseudomonas* having a genome into which the nucleic acid fragment is integrated.

In some embodiments of the present application, the *Escherichia coli* is strain S17-1.

In some embodiments of the present application, the *Pseudomonas* is strain PE1668.

In a fifth aspect of the present application, a viscous PHA is provided, which has the following structural formula:

In a sixth aspect of the present application, use of the viscous PHA in preparation of a degradable product is provided.

In a seventh aspect of the present application, a degradable product is provided, which includes the viscous PHA.

In an eighth aspect of the present application, use of the mutant, the nucleic acid fragment, the recombinant vector, or the *Escherichia coli* in preparation of the viscous PHA is provided.

In a ninth aspect of the present application, a method for preparing the viscous PHA is provided. The preparation method includes following steps:

inoculating *Pseudomonas* into a fermentation culture medium to perform fermentation culture, harvesting biomass, and extracting the viscous PHA from the biomass.

In some embodiments of the present application, the fermentation culture medium includes 0 g/L to 40 g/L glucose, 0.1 g/L to 5 g/L 10-undecenoic acid, and lysogeny broth (LB) medium.

In some embodiments of the present application, the fermentation culture medium includes 10 g/L to 40 g/L glucose, 1 g/L to 3.5 g/L 10-undecenoic acid, and LB medium.

In some embodiments of the present application, the fermentation culture is performed at a temperature of 28° C. to 42° C. for a time period of 12 hours (h) to 72h with a rotation speed of 150 rpm to 300 rpm.

Details of one or more embodiments of the present application are set forth in the following description, and other features, objectives, and advantages of the present application will become apparent from the specification and claims.

BRIEF DESCRIPTION OF THE DRAWINGS

In order to illustrate the embodiments of the present disclosure more clearly, the drawings used in the embodiments will be described briefly. Apparently, the following described drawings are merely for the embodiments of the present disclosure, and other drawings can be derived by those of ordinary skill in the art without any creative effort.

DETAILED DESCRIPTION

Figure 1:
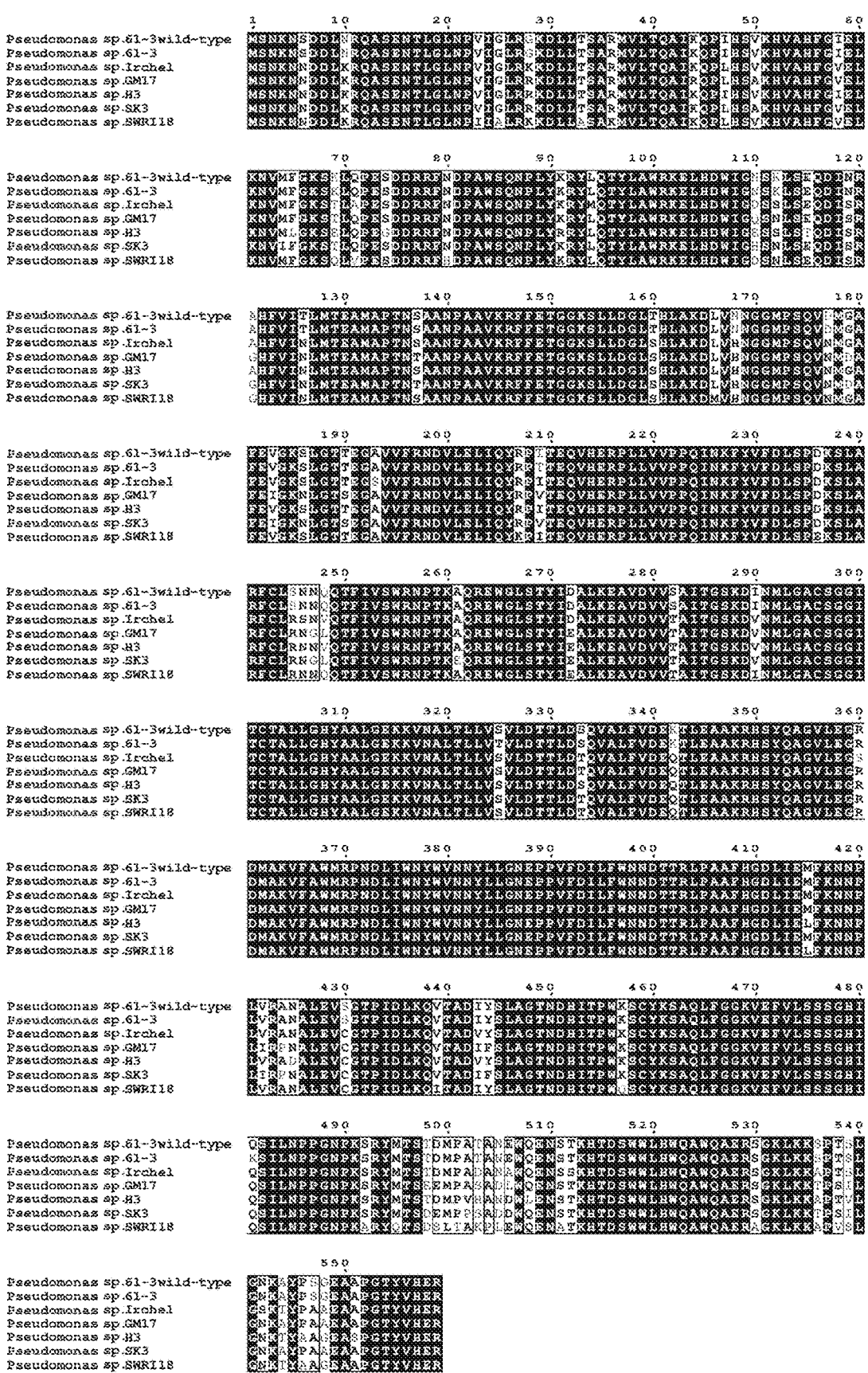
FIG. 1 shows a comparison of protein sequences of PHA polymerases from different bacterial strains, wherein the amino acid sequence of *Pseudomonas* sp. 61-3 is referenced as SEQ ID NO: 9, the amino acid sequence of *Pseudomonas* sp. 61-3wild-type is referenced as SEQ ID NO: 11, the amino acid sequence of *Pseudomonas* sp. Irchel is referenced as SEQ ID NO: 12, the amino acid sequence of *Pseudomonas* sp. H3 is referenced as SEQ ID NO: 13, the amino acid sequence of *Pseudomonas* sp. GM17 is referenced as SEQ ID NO: 14, the amino acid sequence of *Pseudomonas* sp. SK3 is referenced as SEQ ID NO: 15, and the amino acid sequence of *Pseudomonas* sp. SWRI18 is referenced as SEQ ID NO: 16.

The technical solutions in embodiments of the present application will now be clearly and fully described in detail with reference to the accompanying drawings. The embodiments described herein are only some but not all embodiments of the present application. All other embodiments obtained by those of ordinary skill in the art without creative efforts should fall within the scope of protection of the present application.

Unless otherwise defined, all technical and scientific terms used herein have the same meaning as commonly understood by those skilled in the art to which the present application pertains. The terms used in the specification of the present application are merely for the purpose of describing specific embodiments and are not intended to limit the present application.

First Aspect of the Present Application

The present application provides a mutant of PHA polymerase PhaC$_{61-3}$, and the mutant has following amino acid mutation sites: E115T, A261E, R360S, and K457Q. The amino acid sequence of PHA polymerase PhaC$_{61-3}$ is as shown in SEQ ID NO: 9.

Second Aspect of the Present Application

The present application provides a nucleic acid fragment, and the nucleic acid fragment encodes the mutant.

Third Aspect of the Present Application

The present application provides a recombinant vector including the nucleic acid fragment.

Fourth Aspect of the Present Application

The present application provides a genetically engineered bacterium. The bacterium is *Escherichia coli* containing the recombinant vector, or the bacterium is *Pseudomonas* having a genome into which the nucleic acid fragment is integrated.

In some embodiments of the present application, the *Escherichia coli* is strain S17-1.

In some embodiments of the present application, the *Pseudomonas* is strain PE1668.

Fifth Aspect of the Present Application

The present application provides a viscous PHA, which has the following structural formula:

Sixth Aspect of the Present Application

The present application provides use of the viscous PHA in preparation of a degradable product.

Seventh Aspect of the Present Application

The present application provides a degradable product including the viscous PHA.

The degradable product, for example, is a packaging material, a tissue engineering material, a controlled-release material, an electrical material, or a medical material.

Eighth Aspect of the Present Application

The present application provides use of the mutant, the nucleic acid fragment, the recombinant vector, or the *Escherichia coli* in preparation of the viscous PHA.

Ninth Aspect of the Application

The present application provides a method for preparing the viscous PHA, which includes the following steps:

inoculating *Pseudomonas* into a fermentation culture medium to perform fermentation culture, harvesting biomass, and extracting the viscous PHA from the biomass.

In some embodiments, the fermentation culture medium includes 0 g/L to 40 g/L glucose, 0.1 g/L to 5 g/L 10-undecenoic acid, and LB medium. The fermentation culture medium can include glucose or be free of glucose. Glucose can have a concentration (in g/L), such as 0 g/L, 2 g/L, 4 g/L, 6 g/L, 8 g/L, 10 g/L, 12 g/L, 14 g/L, 16 g/L, 18 g/L, 20 g/L, 22 g/L, 24 g/L, 26 g/L, 28 g/L, 30 g/L, 32 g/L, 34 g/L, 36 g/L, 38 g/L, or 40 g/L. 10-undecenoic acid can have a concentration (in g/L) such as 0.1 g/L, 0.5 g/L, 1 g/L, 1.5 g/L, 2 g/L, 2.5 g/L, 3 g/L, 3.5 g/L, 4 g/L, 4.5 g/L, or 5 g/L.

In some embodiments, the fermentation culture medium includes 10 g/L to 40 g/L glucose, 1 g/L to 3.5 g/L 10-undecenoic acid, and LB medium.

In some embodiments, the fermentation culture is performed at a temperature of 28° C. to 42° C. for a time period of 12 hours (h) to 72h with a rotation speed of 150 rpm to 300 rpm. The fermentation temperature (in ° C.) can be such as 28° C., 30° C., 32° C., 34° C., 36° C., 38° C., 40° C., or 42° C. The fermentation time period (in hour) can be such as 12 h, 16 h, 20 h, 24 h, 28 h, 32 h, 36 h, 40 h, 44 h, 48 h, 52 h, 56 h, 60 h, 64 h, 68 h, or 72 h. The rotation speed (in rpm) can be such as 150 rpm, 175 rpm, 200 rpm, 225 rpm, 250 rpm, 275 rpm, or 300 rpm.

The following examples are provided to specifically describe the embodiments of the present application. It should be understood that the examples are for illustration only and not intended to limit the scope of the present application. In the following examples, experimental methods not specifying specific conditions should refer first to the guidance given in the present application, or to the experimental manuals or conventional conditions in the art, or to the conditions recommended by manufacturers, or to the experimental methods known in the art.

In the specific examples described below, the measurement parameters for raw material components may have minor deviations within the range of weighing accuracy unless specifically stated, and the temperature and time parameters may have acceptable deviations due to instrument testing accuracy or operational precision.

Example 1: Genetic Modification of PHA Polymerase (1) Comparison of PHA Polymerase Amino Acid Sequences from Different *Pseudomonas* Strains The protein sequence of PHA polymerase (PhaC$_{61-3}$, from *Pseudomonas* sp.61-3) in recombinant *Pseudomonas* PE1668 (Li M, Ma Y, Zhang X, Zhang L, Chen X, Ye J W, Chen GQ. Tailor-Made Polyhydroxyalkanoates by Reconstructing *Pseudomonas Entomophila*. Adv Mater. 2021 October: 33 (41): e2102766. doi: 10.1002/adma.202102766. Epub 2021 Jul. 28. PMID: 34322928, which is incorporated herein by reference) was analyzed using NCBI Blast to screen out strains with high homology, similar structures, and identical functions: *Pseudomonas* sp. Irchel 3E20, *Pseudomonas* sp. H3, *Pseudomonas* sp. GM17, *Pseudomonas* sp. SK3, and *Pseudomonas* sp. SWRI18. The amino acid sequences of these strains and PhaC$_{61-3}$ were compared using MEGA 6.0 software. The specific comparison results are shown in FIG. 1.

(2) Site-Directed Mutagenesis of PHA Polymerase PhaC$_{61-3}$

The PHA polymerase PhaC$_{61-3}$ (of strain PE1668) has amino acid differences only at positions 325 and 481 as compared to the native sequence of PhaC$_{61-3}$ (from *Pseudomonas* sp. 61-3), but includes more differences as compared to the other strains. For these differences, the following four amino acid sites were mutated: E115T, A261E, R360S, K457Q. Primers were designed as follows for these mutations, and the required gene fragments were obtained and connected using T4 ligase.

(1̂) For the mutation E115T, primers were as follows, designed using Snapgene software:

```
115-F (SEQ ID No. 1):
ACACAGGACATCAATCGCGCTCACTTCGT

115-R (SEQ ID No. 2):
GGACAGTTTGCTGTTGCCGATCCAGTC
```

The reaction system was in a total volume of 50 μL, and includes the following components added in a 0.2 mL PCR tube:

TABLE 1

| Components added into a PCR system for Q5 High-Fidelity DNA Polymerase | |
|---|---|
| System Component | Reaction System |
| Primer 115-F (10 μmol/L) | 2.5 μL |
| Primer 115-R (10 μmol/L) | 2.5 μL |
| Q5 High-Fidelity 2x Master Mix | 25 μL |
| Template DNA (<200 ng) | 1 μL |
| ddH₂O | To 50 μL |

After mixing and instant centrifugation of the above components, PCR were performed under the following reaction parameters: denaturation at 98° C. for 30 seconds (sec); 35 cycles for denaturation at 98° C. for 10 sec, annealing at 72° C. for 30 sec, and extension at 72° C. for 5.5 minutes (min); and a final extension at 72° C. for 2 min. The formed gene fragments were collected using a universal DNA purification kit (purchased from Tiangen Biochemical Technology Co., Ltd.), following the steps provided in the product manual.

The gene fragments were ligated using T4 DNA Ligase (purchased from New England Biolabs) in a reaction system with a total volume of 10 μL, including the following components sequentially added in a 0.2 mL PCR tube:

TABLE 2

| Components added in a PCR system for T4 ligase | |
|---|---|
| System Component | Reaction System |
| T4 DNA Ligase Buffer (10x)* | 0.02-0.5 pmols (<5 μL) |
| PCR DNA blunt-end fragments | 50 ng (0.020 pmol) |
| T4 DNA ligase | 0.5 μL |
| T4 PNK | 0.5 μL |
| Nuclease-Free Water | To 10 μL |

After mixing and instant centrifugation of the above components, the ligation was carried out overnight at 16° C. to obtain Ligated Product 1.

(2̂) For the mutation A261E, the following operations were performed on Ligated Product 1 obtained in step (1̂):

The primer sequences designed using Snapgene software and Q5 system reaction parameters were as follows:

```
261-F (SEQ ID No. 3):
GAACAGCGTGAGTGGGGTCTGTCGA

261-R (SEQ ID No. 4):
CTTGGTCGGGTTGCGCCAGCTGA
```

Reaction parameters: denaturation at 98° C. for 30 sec; 35 cycles for denaturation at 98° C. for 10 sec, annealing at 72° C. for 30 sec, and extension at 72° C. for 5.5 min; and a final extension at 72° C. for 2 min.

The obtained gene fragments were ligated using the T4 DNA ligase in the same method as in step (1̂), resulting in Ligated Product 2.

(3̂) For the mutation R360S, the following operations were performed on Ligated Product 2 obtained in step (2̂):

The primer sequences designed using Snapgene software and Q5 system reaction parameters were as follows:

```
360-F (SEQ ID No. 5):
AGCGACATGGCCAAAGTCTTCGCCTGGA

360-R (SEQ ID No. 6):
GCCTTCCAGCACGCCGGCCTGATA
```

Reaction parameters: denaturation at 98° C. for 30 sec; 35 cycles for denaturation at 98° C. for 10 sec, annealing at 72° C. for 30 sec, and extension at 72° C. for 5.5 min, and a final extension at 72° C. for 2 min.

The obtained gene fragments were ligated using the T4 DNA ligase in the same method as in step (1̂), resulting in Ligated Product 3.

④ For the mutation K457Q, the following operations were performed on Ligated Product 3 obtained in step ③:

The primer sequences designed using Snapgene software and Q5 system reaction parameters were as follows:

```
457-F (SEQ ID No. 7):
CAGTCTTGCTACAAGTCGGCGCAACTGTTCGG

457-R (SEQ ID No. 8):
CCAGGGCGTGATGTGATCGTTGGTGCC
```

Reaction parameters: denaturation at 98° C. for 30 sec; 35 cycles for denaturation at 98° C. for 10 sec, annealing at 72° C. for 30 sec, and extension at 72° C. for 5.5 min; and a final extension at 72° C. for 2 min.

The obtained gene fragments were ligated using the T4 DNA ligase in the same method as in step ①, to finally obtain Ligated Product 4.

(3) Preparation of *Escherichia coli* S17-1 Competent Cells

① A LB culture plate was used, and *Escherichia coli* S17-1 (preserved at −80° C. in glycerol) was picked with an inoculating loop and streaked into the plate, which was incubated at 37° C. for 20 h to 24 h.

② A single colony of *Escherichia coli* S17-1 was picked from the LB plate and inoculated into a shake tube (5 mL of LB liquid medium) and incubated with shaking at 37° C. for 12 h.

③ The above culture was inoculated into a 150 ml conical flask (LB liquid medium) at 1% (v/v), incubated with shaking at 37° C. until OD600 reaches 0.4 to 0.5, then placed on ice to halt the growth.

④ 1 mL of the above culture was transferred into a 1.5 mL centrifuge tube, centrifuged at 4000 rpm, 4° C. for 10 min, then the supernatant was discarded; then operations followed the instructions of the *E. coli* Competent Cell Preparation Kit (by Takara Company).

⑤ The competent cells were divided into 50 μL/tube on ice, stored at −80° C., thus obtaining *Escherichia coli* S17-1 competent cells.

(4) Transformation of Ligated Product into *Escherichia coli* S17-1

① 50 μL of *Escherichia coli* S17-1 competent cells was taken and thaw on ice, added with 5 μL of the final Ligated Product 4 including all four amino acid mutations from step (2), gently mixed, and left on ice for 30 min.

② The mixture was heat shocked at 42° C. for 60 sec in a water bath, then the tube was quickly transferred to an ice bath for 2 min stay.

③ 500 μL of sterile LB liquid medium (without antibiotics) was added to the mixture, mixed well and incubated at 37° C., 220 rpm for 1 h.

④ 200 μL of the culture from step 3 was spread onto an LB plate containing kanamycin, and incubated at 37° C. for 16 h.

⑤ A positive single colony was picked and inoculated into a shake tube containing LB liquid medium (5 mL, supplemented with 1% % kanamycin), incubated overnight at 37° C., 220 rpm. The positive single colony was verified by PCR of the culture and sent to Sangon Biotech (Shanghai) Co., Ltd. for sequencing analysis. Sequence alignment confirmed the successful construction of the recombinant plasmid.

(5) Conjugation between *Escherichia coli* S17-1 and *Pseudomonas*

① *Escherichia coli* S17-1 and *Pseudomonas entomophila* LAC32 cultures, 50 μL for each, were dropped onto a LB plate, and incubated at 30° C. for 10 h.

② The cultures on the plate were streaked with a pipette tip in a grid pattern (three lines horizontally and three lines vertically), then spread onto an LB plate containing kanamycin (Kan) and chloramphenicol (Cm) using the same pipette tip: then the present plate was added with 200 μL of LB liquid medium, which was spread using a spreading rod, and the plate was incubated at 30° C. for 48 h.

③ The positive monoclonal colonies grown in the plate were streaked onto another LB plate containing Kan and incubated at 30° C. for 24 hours.

④ A single colony was picked and inoculated into a shake tube containing 5 mL LB liquid medium with Kan, incubated at 30° C., 220 rpm for 12 h. The recombinant *Pseudomonas*, named PE1668-1, was stored at −80° C. in 50% glycerol for future use.

Example 2: Fermentation Production of Novel, Viscous PHA (P (3HB-co-3HU10D))

The fermentation production of this novel material was carried out using the recombinant *Pseudomonas* PE1668-1 containing the plasmid, obtaining wet bacterial biomass containing PHA (P (3HB-co-3HU10D)).

(1) Preparation of Seed Culture

① Monoclonal Colonies: the above recombinant strain PE1668-1 was streaked using an inoculating loop onto an LB plate containing Kan on a clean bench. The plate was incubated at 30° C. for 24 h to allow for the growth of monoclonal colonies.

② Primary Seed Culture: a monoclonal colony from step ① was picked and inoculated into a shake tube containing 5 mL of seed culture medium (LB+1% % Kan), and cultured at 30° C., 200 rpm for 12 h.

③ Secondary Seed Culture: 200 μL (1% inoculum, v/v) of the culture from step 2 was inoculated into a 150 ml conical flask containing 20 mL of seed culture medium (LB+1% o Kan), and incubated at 30° C., 200 rpm for 12 h.

(2) Preparation of Fermentation Broth

LB Medium: yeast powder 5 g/L: tryptone 10 g/L: sodium chloride 10 g/L;

Carbon Source: glucose 17 g/L to 30 g/L: 10-undecenoic acid 1 g/L to 3.2 g/L:

Antibiotic: kanamycin (Kan):

(3) Fermentation Culture

The seed culture was inoculated at 5% (v/v) into a 2L shake flask containing 400 mL of the LB medium, and 1% % Kan antibiotic, various concentrations of carbon source, and the seed culture were sequentially added. The culture system was incubated at 30° C., 200 rpm for 48 h.

(4) Measurement of Cell Dry Weight and PHA (P (3HB-co-3HU10D)) Content

Cell Dry Weight (CDW): 25 mL of the post-fermentation culture was transferred into a 50 mL centrifuge tube, and centrifuged at 8000 rpm at room temperature for 6 min. The supernatant was discarded, and the precipitate was washed with deionized water twice, frozen in a refrigerator at −80° C. for 1 h, lyophilized in a vacuum freeze-dryer for 18 h, and weighed. The CDW (g/L) was calculated by dividing the resulted weight by the original volume of the culture.

PHA (P (3HB-co-3HU10D)) Content Measurement: 40 mg of the weighed lyophilized cells was added with 2 mL of esterification liquid (containing methanol, 3% (v/v) concentrated sulfuric acid (98%, w/w), and 1 g/L benzoic acid) and 2 mL chloroform, and esterified at 100° C. for about 4 h. 25 mg of a standard PHA with the same treatments was used for reference. Subsequently, the PHA content was measured using a GC-2014 gas chromatograph (Shimadzu, Japan). The test method was as follows: initial temperature was 80° C. and maintained for 1.5 min; in the first phase, the temperature was increased to 140° C. at a rate of 30° C./min; in the second phase, the temperature was increased to 240° C. at a rate of 40° C./min, which took 2 min: the total analysis time was 8 minutes; the injection temperature was 240° C. and the detector temperature was 250° C.

(5) Fermentation Results

The fermentation results and the content of PHA (P (3HB-co-3HU10D)) vary with different concentrations of 10-undecenoic acid and glucose, as shown in Table 3 (all data in the table are presented as mean±variance):

TABLE 3

| Fermentation Results with Different Concentrations of 10-Undecenoic Acid and Glucose | | | | |
|---|---|---|---|---|
| Test No. | Glucose (g/L) | 10-Undecenoic Acid (g/L) | CDW (g/L) | PHA (P(3HB-co-3HU10D)) Content (%) |
| 1-1 | 30 | 1 | 5.974 ± 0.531 | 77.4 ± 0.401 |
| 1-2 | 34 | 2 | 6.5 ± 0.481 | 79.8 ± 0.061 |
| 1-3 | 20 | 2 | 5.854 ± 0.288 | 73.268 ± 0.333 |
| 1-4 | 25 | 2.5 | 6.413 ± 0.145 | 75.61 ± 0.404 |
| 1-5 | 10 | 2.5 | 3.697 ± 0.514 | 60.967 ± 0.676 |
| 1-6 | 17 | 3.2 | 3.986 ± 0.169 | 63.633 ± 0.277 |

Example 3: Extraction and Purification of Novel, Viscous PHA (P (3HB-co-3HU10D))

(1) Extraction of Novel, Viscous PHA (P (3HB-co-3HU10D))

Ⅰ Obtaining Wet Bacterial Biomass:

The *Pseudomonas* culture after the fermentation in Example 2, step (3) was collected and poured into a 50 mL centrifuge tube, and centrifuged at room temperature for 6 min at 8000 rpm. The supernatant was discarded carefully so as not to lose the precipitate, which was then added with deionized water to resuspend, and centrifuged at room temperature for 6 min at 8000 rpm, and this process was repeated twice.

Disruption of *Pseudomonas* Cells and Extraction of PHA (P (3HB-co-3HU10D))

Cell disruption was achieved using the aqueous phase separation method, wherein a beaker containing the treated bacterial suspension was heated, and once the temperature reached 50° C., 1 mg/mL surfactant was added and the pH was maintained at about 9 with 5M NaOH for 15 min, during which the suspension was stirred continuously.

After cooling to room temperature, the mixture was transferred into multiple 50 mL centrifuge tubes and centrifuged at room temperature for 6 min at 8000 rpm. The supernatant was discarded while minimizing loss of precipitate. 30 mL deionized water was added to resuspend the precipitate while ensuring complete dissolution of the precipitate, The resuspension was centrifuged at room temperature for 6 min at 8000 rpm, and the supernatant was discarded; and this process was repeated twice. The crude PHA (P (3HB-co-3HU10D)) product was frozen at −80° C. for 0.5 h, and lyophilized in a vacuum freeze-dryer for 10 h, and the final product was then weighed.

(2) Purification of Novel, Viscous PHA (P (3HB-co-3HU10D))

The extraction and purification of the obtained PHA material were performed according to the method described in the reference Follonier, S., Riesen, R., & Zinn, M. (2015), Pilot-scale Production of Functionalized mcl-PHA from Grape Pomace Supplemented with Fatty Acids, Chemical and Biochemical Engineering Quarterly, 29, 113-121, which is incorporated herein by reference. The method for extraction and purification involved initially using dichloromethane for extraction on the crude PHA product, followed by precipitation and purification with cold methanol. Specifically, the weighed crude PHA product was added with dichloromethane at a ratio of 1 g/17 ml, stirred continuously, and then allowed to settle for 3 h.

The mixture was suction filtered to remove the residue, retaining the filtrate containing the PHA material in a suitable beaker. While stirring continuously, cold methanol was added dropwise to methanol volume/dichloromethane volume containing PHA being 5:1. In this process precipitation of the material can be observed. The solution was left to settle for 1 h, filtered to retain the PHA material, which was then redissolved in dichloromethane and dried in a vacuum dryer for 24 h to obtain the final PHA material.

(3) Measurement of the Content and Quantity of Novel, Viscous PHA (P (3HB-co-3HU10D))

Ⅰ Measurement of PHA (P (3HB-co-3HU10D)) Content: The content was determined using gas chromatography, similar to Example 2.

② Measurement of PHA (P (3HB-co-3HU10D)) Quantity: Considering the viscosity of the material, during purification, the material was disposed in a glass dish or a beaker for evaporation. The mass of the material can be determined by the change in mass $\Delta m$, where $\Delta m = m_{total} - m_0$, $m_{total}$ is the total mass of the material and the glass dish or beaker, and $m_0$ is the mass of the glass dish or beaker.

(4) Quantity of Purified Novel, Viscous PHA (P (3HB-co-3HU10D)) Product

The quantity of the purified PHA product is shown in Table 4. The Test No. correspond to the fermentation results in Table 3 (For example, 2-1 in Table 4 corresponds to 1-1 in Table 3), and the data in the table are presented as mean±variance.

TABLE 4

| | Quantity of the Extracted and Purified Novel, Viscous PHA (P(3HB-co-3HU10D)) Product | | |
|---|---|---|---|
| Test No. | Mass after Cell Disruption (g/L) | Mass after Purification/Mass after Cell Disruption (g/g) | PHA (P(3HB-co-3HU10D)) Purity (%) |
| 2-1 | 3.8 | 0.55 | 91.430 ± 0.457 |
| 2-2 | 4.2 | 0.62 | 89.412 ± 0.033 |
| 2-3 | 3.6 | 0.48 | 91.333 ± 0.297 |
| 2-4 | 4.0 | 0.54 | 90.505 ± 0.601 |
| 2-5 | 1.6 | 0.45 | 91.570 ± 0.288 |
| 2-6 | 1.9 | 0.59 | 90.067 ± 0.271 |

Example 4: Nuclear Magnetic Resonance Analysis and Viscosity Testing of Novel, Viscous PHA (P (3HB-co-3HU10D))

(1) Nuclear Magnetic Resonance (NMR) Analysis

Figure 2:
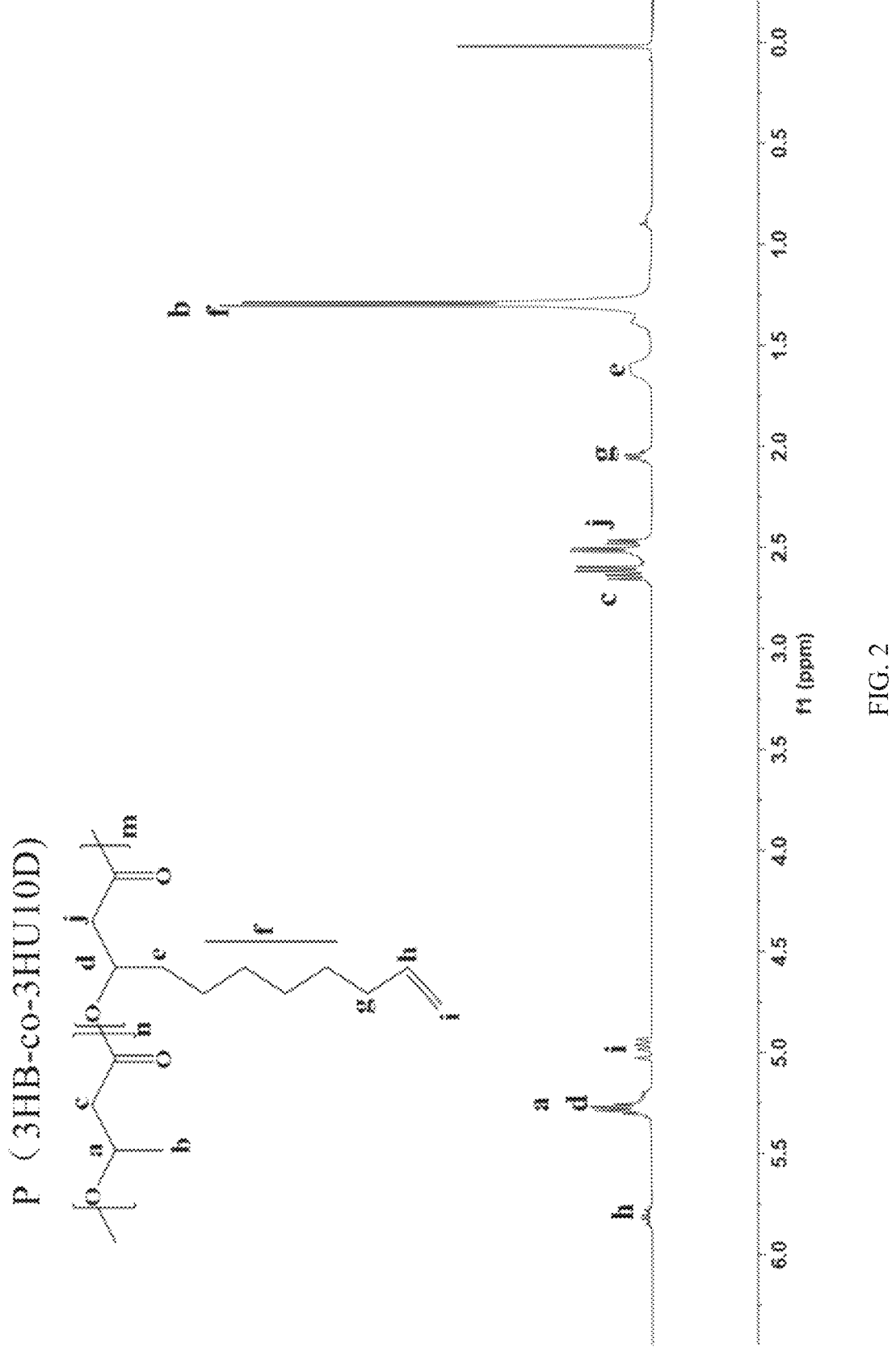
FIG. 2 shows $^1$HNMR spectrum of P (3HB-co-3HU10D) with a ratio of 15% to 25% of monomer 3HU10D.

The PHA (P (3HB-co-3HU10D)) material extracted and purified in Example 3 was subjected to NMR analysis to determine the proportion of each monomer. As the ratio of the PHA (P (3HB-co-3HU10D)) material varies with different raw material ratios:

When the glucose content was 30 g/L to 34 g/L, and the 10-undecenoic acid content was 1 g/L to 2 g/L, the 3HU10D monomer can reach 15% to 25%. The $^1$HNMR result is shown in FIG. 2.

Figure 3:
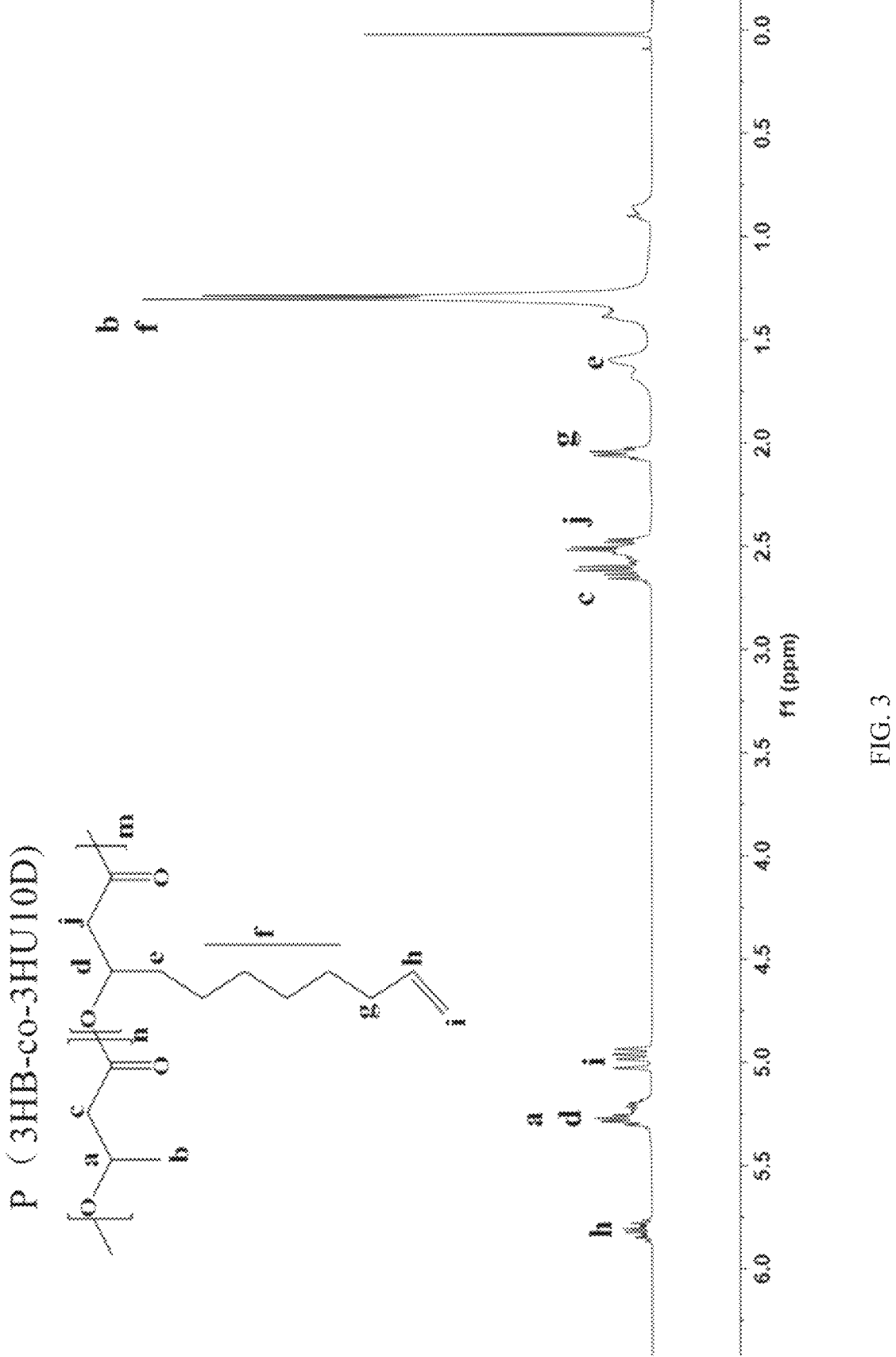
FIG. 3 shows $^1$HNMR spectrum of P (3HB-co-3HU10D) with a ratio of 30% to 40% of monomer 3HU10D.

When the glucose content was 20 g/L to 25 g/L, and the 10-undecenoic acid content was 2 g/L to 2.5 g/L, the 3HU10D monomer can reach 30% to 40%. The $^1$HNMR result is shown in FIG. 3.

Figure 4:
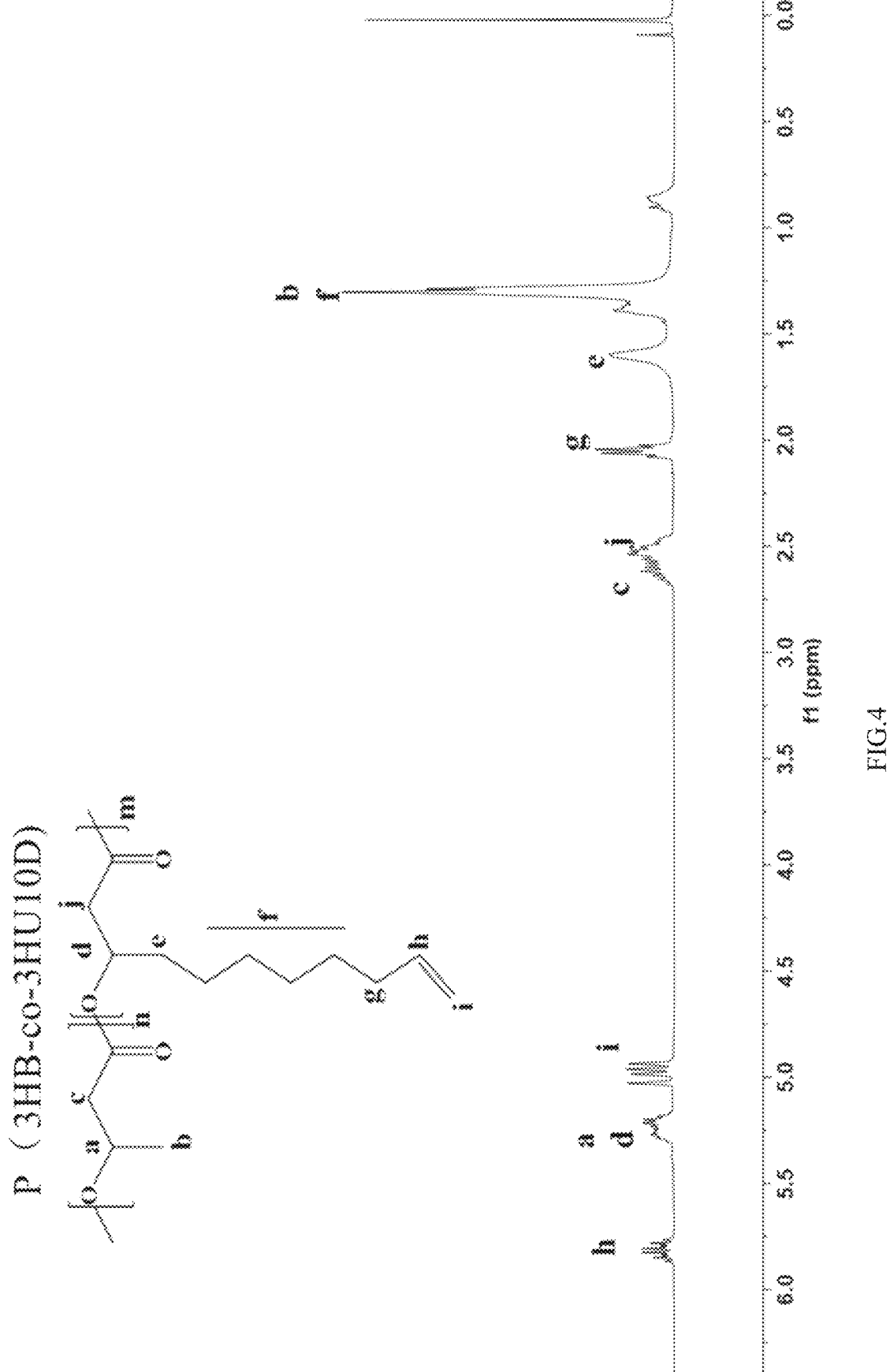
FIG. 4 shows $^1$HNMR spectrum of P (3HB-co-3HU10D) with a ratio of 45% to 50% of monomer 3HU10D.

When the glucose content was 10 g/L to 17 g/L, and the 10-undecenoic acid content was 2.5 g/L to 3.2 g/L, the 3HU10D monomer can reach 45% to 50%. The $^1$HNMR result is shown in FIG. 4.

(2) Viscosity Analysis

Figure 5:
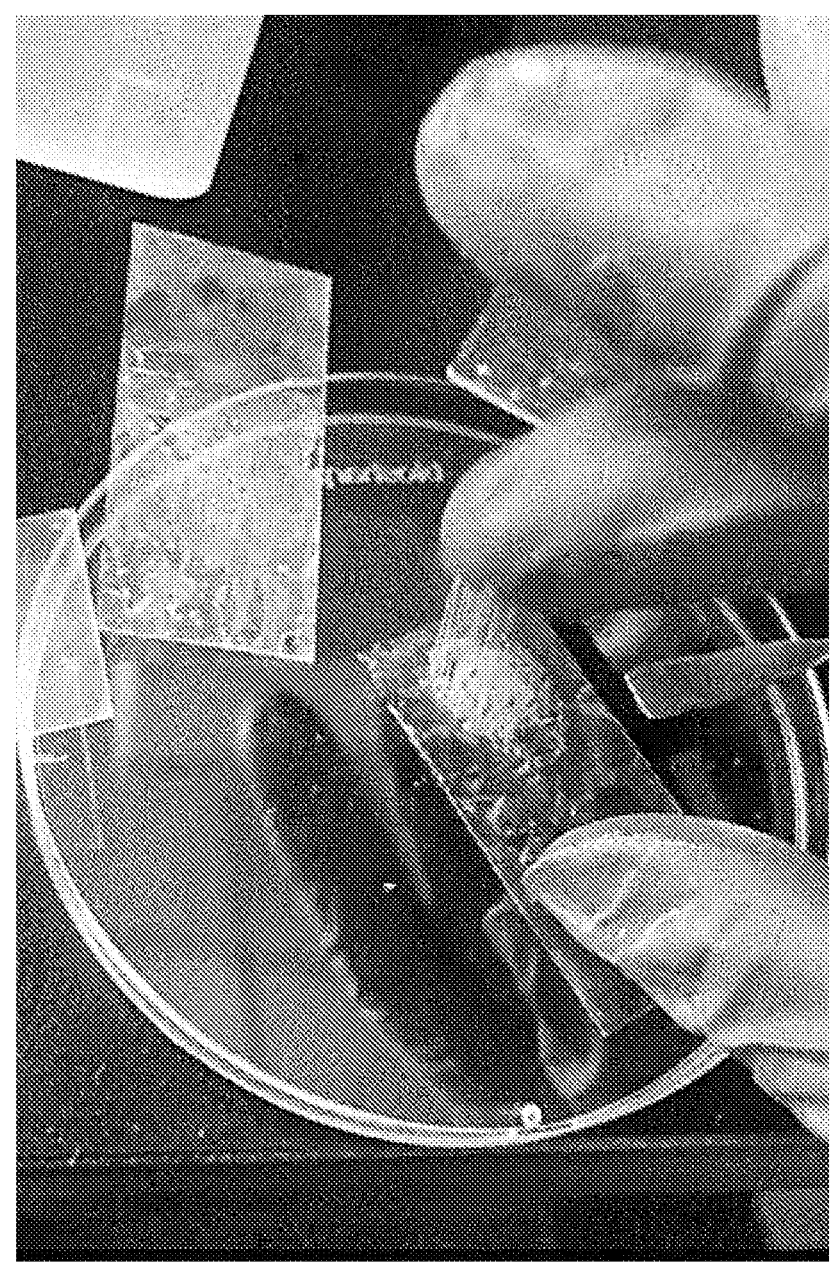
FIG. 5 shows viscosity of P (3HB-co-3HU10D) material.

In Example 3, the purified material P (3HB-co-3HU10D) exhibited transparent and viscous characteristics, as shown in FIG. 5 (corresponding to Test Nos. 2-3), clearly demonstrating the viscosity of the P (3HB-co-3HU10D) material.

Figure 6:
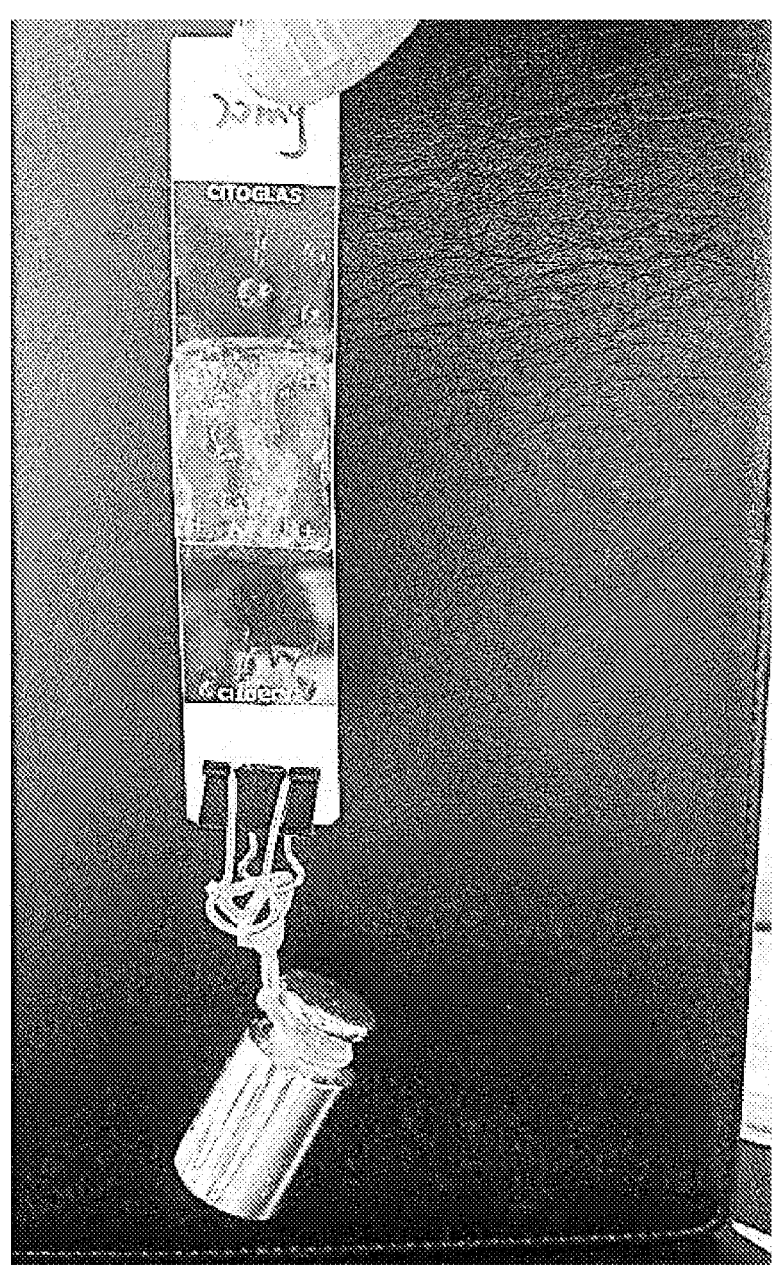
FIG. 6 shows a viscosity test of P (3HB-co-3HU10D) material with a ratio of 30% to 40% of monomer 3HU10D.

Viscosity Testing: 20 mg of the material was applied evenly on one side of a glass sheet A, and pressed with another clean glass sheet B, ensuring that both glass sheets and the material therebetween were in close contact; then a 0.1 g weight was hung on the other side of the glass sheet B using a clip and a rubber band; after assembly, the two glass sheets were vertically arranged and the weight was continuously changed until the glass sheets A and B start to separate. Referring to FIG. 6, corresponding to Test No. 2-3.

The viscosity test on 20 mg of P (3HB-co-3HU10D) materials with different 3HU10D monomer contents was performed, and the maximum weights the material can withstand are as follows (Table 5):

TABLE 5

| | Maximum Weight Withstood by P(3HB-co-3HU10D) Material with Different 3HU10D Monomer Proportion | |
|---|---|---|
| 3HU10D Proportion in P(3HB-co-3HU10D) | Mass (mg) | Maximum Weight Withstood by Material (kg) |
| 15% to 25% (2-1 and 2-2) | 20 | 0.357 ± 0.186 |
| 30% to 40% (2-3 and 2-4) | 20 | 1.373 ± 0.343 |
| 45% to 50% (2-5 and 2-6) | 20 | 1.667 ± 0.167 |

The above data indicate that the higher the proportion of the 3HU10D monomer in the PHA, the greater the viscosity of the material, and the greater the maximum weight the material can withstand. When the proportion of the 3HU10D monomer is above 45%, the maximum weight the material can withstand is 1.67 kg.

(3) Underwater Viscosity Analysis

①̂ Underwater Viscosity Analysis with Different Carriers:

The PHA materials with different 3HU10D proportions obtained in Example 3 were analyzed for underwater viscosity.

Different adhered carriers were used for underwater viscosity testing: 20 mg of the 5 material was each applied evenly on glass sheets, metal sheets, plastic sheets, collagen films, and PVA films of the same size, which were then disposed respectively in beakers containing deionized water (at room temperature) for a duration of 0.5 h, followed by the viscosity testing method described in (2).

Underwater viscosity tests were carried out on 20 mg of P (3HB-co-3HU10D) material with different 3HU10D monomer contents, with the maximum weight tolerance as follows (Table 6):

TABLE 6

| | Maximum Weight Withstood by P(3HB-co-3HU10D) Material with Different 3HU10D Monomer Proportion | |
|---|---|---|
| Carrier | 3HU10D Proportion in P(3HB-co-3HU10D) | Maximum Weight Withstood by Material (kg) |
| Glass Sheet | 15% to 25% | 0.157 ± 0.126 |
| Glass Sheet | 30% to 40% | 1.073 ± 0.371 |
| Glass Sheet | 45% to 50% | 1.467 ± 0.158 |
| Metal Sheet | 15% to 25% | 0.109 ± 0.526 |
| Metal Sheet | 30% to 40% | 0.774 ± 0.971 |
| Metal Sheet | 45% to 50% | 1.081 ± 0.732 |
| Plastic Sheet | 15% to 25% | 0.097 ± 0.462 |
| Plastic Sheet | 30% to 40% | 0.773 ± 0.139 |
| Plastic Sheet | 45% to 50% | 1.008 ± 0.858 |
| Collagen Film | 15% to 25% | 0.279 ± 0.076 |
| Collagen Film | 30% to 40% | 1.163 ± 0.813 |
| Collagen Film | 45% to 50% | 1.472 ± 0.023 |
| PVA Film | 15% to 25% | 0.198 ± 0.466 |
| PVA Film | 30% to 40% | 0.993 ± 0.294 |
| PVA Film | 45% to 50% | 1.425 ± 0.788 |

The above data indicate that for the same carrier, the lower the proportion of the 3HU10D monomer, the less the maximum weight the material can withstand; for the same proportion of the 3HU10D monomer, the collagen film as a carrier can withstand the greatest weight, the PVA film is the second, and the glass sheet also shows significant viscosity.

2 Underwater Viscosity Testing at Different Temperatures:

20 mg of the material was each evenly applied on glass sheets, collagen films, and PVA films of the same size, which were then disposed respectively in beakers containing deionized water at different temperatures for a duration of 0.5 h, followed by the viscosity testing method described in (2).

The maximum weight tolerance at different conditions is as follows (Table 7):

TABLE 7

| | | Maximum Weight Withstood by P(3HB-co-3HU10D) Material with Different 3HU10D Monomer Proportion | |
| Carrier | Temperature (° C.) | 3HU10D Proportion in P(3HB-co-3HU10D) | Maximum Weight Withstood by Material (kg) |
| --- | --- | --- | --- |
| Glass Sheet | 20 | 15% to 25% | 0.104 ± 0.009 |
| Glass Sheet | 20 | 30% to 40% | 0.998 ± 0.581 |
| Glass Sheet | 20 | 45% to 50% | 1.298 ± 0.681 |
| Glass Sheet | 37 | 15% to 25% | 0.187 ± 0.421 |
| Glass Sheet | 37 | 30% to 40% | 1.123 ± 0.862 |
| Glass Sheet | 37 | 45% to 50% | 1.392 ± 0.318 |
| Glass Sheet | 50 | 15% to 25% | 0.099 ± 0.124 |
| Glass Sheet | 50 | 30% to 40% | 0.563 ± 0.338 |
| Glass Sheet | 50 | 45% to 50% | 1.002 ± 0.346 |
| Collagen Film | 20 | 15% to 25% | 0.184 ± 0.639 |
| Collagen Film | 20 | 30% to 40% | 1.078 ± 0.371 |
| Collagen Film | 20 | 45% to 50% | 1.382 ± 0.492 |
| Collagen Film | 37 | 15% to 25% | 0.289 ± 0.622 |
| Collagen Film | 37 | 30% to 40% | 1.396 ± 0.038 |
| Collagen Film | 37 | 45% to 50% | 1.592 ± 0.284 |
| Collagen Film | 50 | 15% to 25% | 0.105 ± 0.632 |
| Collagen Film | 50 | 30% to 40% | 0.773 ± 0.069 |
| Collagen Film | 50 | 45% to 50% | 1.212 ± 0.926 |
| PVA Film | 20 | 15% to 25% | 0.122 ± 0.179 |
| PVA Film | 20 | 30% to 40% | 1.008 ± 0.442 |
| PVA Film | 20 | 45% to 50% | 1.311 ± 0.993 |
| PVA Film | 37 | 15% to 25% | 0.257 ± 0.668 |
| PVA Film | 37 | 30% to 40% | 1.255 ± 0.482 |
| PVA Film | 37 | 45% to 50% | 1.492 ± 0.183 |
| PVA Film | 50 | 15% to 25% | 0.097 ± 0.432 |
| PVA Film | 50 | 30% to 40% | 0.668 ± 0.368 |
| PVA Film | 50 | 45% to 50% | 1.113 ± 0.684 |

The above data indicate that for the same carrier and at the same temperature, the higher the proportion of the 3HU10D monomer, the greater the maximum weight the material can withstand; for the same proportion of the 3HU10D monomer, the collagen film as a carrier at a temperature of 37° C. can withstand the greatest weight, and the PVA film is the second.

SEQ ID No. 9:
MSNKNSDDLNRQASENTLGLNPVIGLRGKDLLTSARMVLTQAIKQPIHS

VKHVAHFGIELKNVMFGKSKLQPESDDRRENDPAWSQNPLYKRYLQTYL

AWRKELHDWIGNSKLSEQDINRAHFVITLMTEAMAPTNSAANPAAVKRF

FETGGKSLLDGLTHLAKDLVNNGGMPSQVDMGAFEVGKSLGTTEGAVVF

RNDVLELIQYRPTTEQVHERPLLVVPPQINKFYVFDLSPDKSLARFCLS

NNQQTFIVSWRNPTKAQREWGLSTYIDALKEAVDVVSAITGSKDINMLG

ACSGGITCTALLGHYAALGEKKVNALTLLVTVLDTTLDSQVALFVDEKT

LEAAKRHSYQAGVLEGRDMAKVFAWMRPNDLIWNYWVNNYLLGNEPPVF

DILFWNNDTTRLPAAFHGDLIEMFKNNPLVRANALEVSGTPIDLKQVTA

-continued

DIYSLAGTNDHITPWKSCYKSAQLFGGKVEFVLSSSGHIKSILNPPGNP

KSRYMTSTDMPATANEWQENSTKHTDSWWLHWQAWQAERSGKLKKSPTS

LGNKAYPSGEAAPGTYVHER.

SEQ ID NO: 10:
MSNKNSDDLNRQASENTLGLNPVIGLRGKDLLTSARMVLTQAIKQPIHS

VKHVAHFGIELKNVMFGKSKLQPESDDRRFNDPAWSQNPLYKRYLQTYL

AWRKELHDWIGNSKLSTQDINRAHFVITLMTEAMAPTNSAANPAAVKRF

FETGGKSLLDGLTHLAKDLVNNGGMPSQVDMGAFEVGKSLGTTEGAVVF

RNDVLELIQYRPTTEQVHERPLLVVPPQINKFYVFDLSPDKSLARFCLS

NNQQTFIVSWRNPTKEQREWGLSTYIDALKEAVDVVSAITGSKDINMLG

ACSGGITCTALLGHYAALGEKKVNALTLLVTVLDTTLDSQVALFVDEKT

LEAAKRHSYQAGVLEGSDMAKVFAWMRPNDLIWNYWVNNYLLGNEPPVF

DILFWNNDTTRLPAAFHGDLIEMFKNNPLVRANALEVSGTPIDLKQVTA

DIYSLAGTNDHITPWQSCYKSAQLFGGKVEFVLSSSGHIKSILNPPGNP

KSRYMTSTDMPATANEWQENSTKHTDSWWLHWQAWQAERSGKLKKSPTS

LGNKAYPSGEAAPGTYVHER.

-continued

SEQ ID NO: 11:
MSNKNSDDLNRQASENTLGLNPVIGLRGKDLLTSARMVLTQAIKQPIHS

VKHVAHFGIELKNVMFGKSKLQPESDDRRFNDPAWSQNPLYKRYLQTYL

AWRKELHDWIGNSKLSEQDINRAHFVITLMTEAMAPTNSAANPAAVKRF

FETGGKSLLDGLTHLAKDLVNNGGMPSQVDMGAFEVGKSLGTTEGAVVF

RNDVLELIQYRPTTEQVHERPLLVVPPQINKFYVFDLSPDKSLARFCLS

NNQQTFIVSWRNPTKAQREWGLSTYIDALKEAVDVVSAITGSKDINMLG

ACSGGITCTALLGHYAALGEKKVNALTLLVSVLDTTLDSQVALFVDEKT

LEAAKRHSYQAGVLEGRDMAKVFAWMRPNDLIWNYWVNNYLLGNEPPVF

DILFWNNDTTRLPAAFHGDLIEMFKNNPLVRANALEVSGTPIDLKQVTA

DIYSLAGTNDHITPWKSCYKSAQLFGGKVEFVLSSSGHIQSILNPPGNP

KSRYMTSTDMPATANEWQENSTKHTDSWWLHWQAWQAERSGKLKKSPTS

LGNKAYPSGEAAPGTYVHER.

SEQ ID NO: 12:
MSNKNNDDLKRQASENTLGLNPVIGLRKKDLLTSARMVLTQAIKQPLHS

VKHVAHFGVELKNVMFGKSTLAPESDDRRFNDPAWSQNPLYKRYMQTYL

AWRKELHDWIGDSSLSEQDISRAHFVINLMTEAMAPTNSAANPAAVKRF

FETGGKSLLDGLSHLAKDLVHNGGMPSQVNMGAFEVGKSLGTTEGSVVF

RNDVLELIQYRPITEQVHERPLLVVPPQINKFYVFDLSPDKSLARFCLR

SNVQTFIVSWRNPTKAQREWGLSTYIDALKEAVDVVTAITGSKDVNMLG

ACSGGITCTALLGHYAALGEKKVNALTLLVSVLDTTLDTQVALFVDEQT

LEAAKRHSYQAGVLEGSDMAKVFAWMRPNDLIWNYWVNNYLLGNEPPVF

DILFWNNDTTRLPAAFHGDLIEMFKNNPLVRANALEVCGTPIDLKQVTA

DVYSLAGTNDHITPWKSCYKSAQLFGGKVEFVLSSSGHIQSILNPPGNP

KSRYMTSTDMPADANAWQENSSKHTDSWWLHWQAWQAERSGKLKKAPTS

LGSKTYPAAEAAPGTYVHER.

SEQ ID NO: 13:
MSNKNNDDLKRQASENTLGLNPVIGLRRKDLLTSARMVLTQAIKQPIHS

VKHVAHFGIELKNVMLGKSELQPEGDDRRFNDPAWSQNPLYRRYLQTYL

AWRKELHDWIGESSLSTQDISRAHFVINLMTEAMAPTNSAANPAAVKRF

FETGGKSLLDGLSHLAKDLVHNGGMPSQVNMGAFEVGKSLGTTEGAVVF

RNDVLELIQYRPITEQVHERPLLVVPPQINKFYVFDLSPDKSLARFCLR

NNVQTFIVSWRNPTKAQREWGLSTYIEALKEAVDVVTAITGSKDVNMLG

ACSGGITCTALLGHYAALGEKKVNALTLLVSVLDTTLDSQVALFVDEQT

LEAAKRHSYQAGVLEGRDMAKVFAWMRPNDLIWNYWVNNYLLGNEPPVF

DILFWNNDTTRLPAAFHGDLIELFKNNPLVRADALEVCGTPIDLKQVTA

DVYSLAGTNDHITPWKSCYKSAQLFGGKVEFVLSSSGHIQSILNPPGNP

KSRYMTSTDMPVHANDWLENSTKHTDSWWLHWQAWQAERSGKLKKAPTV

LGNKTYAAGEASPGTYVHER.

SEQ ID NO: 14:
MSNKNNDDLKRQASENTLGLNPVIGLRRKDLLTSARMVLTQAIRQPLHS

AKHVAHFGVELKNVMFGKSTLQPESDDRRENDPAWSQNPLYKRYLQTYL

-continued
AWRKELHDWIGQSNLSEQDISRGHFVINLMTEAMAPTNTAANPAAVKRF

FETGGKSLLDGLSHLAKDLVHNGGMPSQVNMDAFEIGKNLGTSEGAVVF

RNDVLELIQYRPVTEQVHERPLLVVPPQINKFYVFDLSPDKSLARFCLR

NGLQTFIVSWRNPTKAQREWGLSTYIEALKEAVDVVTAITGSKDVNMLG

ACSGGITCTALLGHYAALGEKKVNALTLLVSVLDTTLDTQVALFVDEQT

LEAAKRHSYQAGVLEGRDMAKVFAWMRPNDLIWNYWVNNYLLGNEPPVF

DILFWNNDTTRLPAAFHGDLIEMFKNNPLIRPNALEVCGTPIDLKQVTA

DIFSLAGTNDHITPWKSCYKSAQLFGGKVEFVLSSSGHIQSILNPPGNP

KSRYMTSEEMPASADLWQENSTKHTDSWWLHWQAWQAERSGKLKKTPSI

LGNKAYPAAEAAPGTYVHER.

SEQ ID NO: 15:
MSNKNNDDLKRQASENTLGLNPVIGLRRKDLLTSARMVLTQAIKQPLHS

AKHVAHFGVELKNVIFGKSTLQPESDDRRENDPAWSQNPLYKRYLQTYL

AWRKELHDWIGHSNLSEQDISRGHFVINLMTEAMAPTNTAANPAAVKRF

FETGGKSLLDGLSHLAKDLVHNGGMPSQVNMDAFEIGKNLGTSEGAVVF

RNDVLELIQYRPVTEQVHERPLLVVPPQINKFYVFDLSPDKSLARFCLR

NGLQTFIVSWRNPTKEQREWGLSTYIEALKEAVDVVTAITGSKDVNMLG

ACSGGITCTALLGHYAALGEKKVNALTLLVSVLDTTLDTQVALFVDEQT

LEAAKRHSYQAGVLEGRDMAKVFAWMRPNDLIWNYWVNNYLLGNEPPVF

DILFWNNDTTRLPAAFHGDLIEMFKNNPLIRPNALEVCGTPIDLKQVTA

DIFSLAGTNDHITPWKSCYKSAQLFGGKVEFVLSSSGHIQSILNPPGNP

KSRYMTSDEMPPSADDWQENSTKHTDSWWLHWQAWQAERSGKLKKTPSI

LGNKAYPAAEAAPGTYVHER.

SEQ ID NO: 16:
MSNKNNDDLKRQASENTLGLNPIIALRKKDLLASAKMVLTQAIKQPLHS

VKHVAHFGVELKNVMFGKSQLVPESDDRRFHDPAWSQNPLYKRYLQTYL

AWRKELHDWIGDSNLSEQDISRGHFVINLMTEAMAPTNSAANPAAVKRF

FETGGKSLLDGLSHLAKDMVHNGGMPSQVNMGAFEVGKSLGTTEGAVVF

RNDVLELIQYKPITEQVHERPLLVVPPQINKFYVFDLSPEKSLARFCLR

NNQQTFIVSWRNPTKAQREWGLSTYIEALKEAVDVVTAITGSKDINMLG

ACSGGITCTALLGHYAALGEKKVNALTLLVSVLDTTLDTQVALFVDEQT

LEAAKRHSYQAGVLEGRDMAKVFAWMRPNDLIWNYWVNNYLLGNEPPVF

DILFWNNDTTRLPAAFHGDLIELFKNNPLVRANALEVCGTPIDLKQITA

DIYSLAGTNDHITPWQSCYKSAQLFGGKVEFVLSSSGHIQSILNPPGNP

KARYQTSDSLTAKPLEWQENATKHTDSWWLHWQAWQAERAGKLKKAPVS

LGNKTYAAGEAAPGTYVHER.

The technical features of the above-mentioned embodiments can be combined arbitrarily. In order to make the description concise, not all possible combinations of the technical features are described in the embodiments. However, as long as there is no contradiction in the combination of these technical features, the combinations should be considered as in the scope of the present disclosure.

The above-described embodiments are only several implementations of the present disclosure, and the descriptions are relatively specific and detailed, but they should not be construed as limiting the scope of the present disclosure. It should be understood by those of ordinary skill in the art that various modifications and improvements can be made without departing from the concept of the present disclosure, and all fall within the protection scope of the present disclosure. Therefore, the patent protection of the present disclosure shall be defined by the appended claims.

What is claimed is:

1. A variant of the polypeptide of SEQ ID NO: 9, wherein the variant has polyhydroxyalkanoate polymerase activity, and the variant comprises all of SEQ ID NO: 9 except for:

a T at the position corresponding to position 115 of SEQ ID NO: 9;

an E at the position corresponding to position 261 of SEQ ID NO: 9;

an S at the position corresponding to position 360 of SEQ ID NO: 9; and a Q at the position corresponding to position 457 of SEQ ID NO: 9.

2. A nucleic acid encoding a variant of the polypeptide of SEQ ID NO: 9, wherein the variant has polyhydroxyalkanoate polymerase activity, and the variant comprises all of SEQ ID NO: 9 except for:

a T at the position corresponding to position 115 of SEQ ID NO: 9;

an E at the position corresponding to position 261 of SEQ ID NO: 9;

an S at the position corresponding to position 360 of SEQ ID NO: 9; and a Q at the position corresponding to position 457 of SEQ ID NO: 9.

3. A recombinant vector comprising the nucleic acid according to claim 2.

4. A genetically engineered bacterium, wherein the genetically engineered bacterium is a genetically engineered *Pseudomonas* that has a genome that comprises the nucleic acid according to claim 2.

5. A genetically engineered bacterium, wherein the genetically engineered bacterium is a genetically engineered *Escherichia coli* transformed with the recombinant vector according to claim 3.

6. A genetically engineered bacterium, wherein the genetically engineered bacterium is an *Escherichia coli* strain S17-1 transformed with the recombinant vector according to claim 3.

7. A nucleic acid encoding a variant of the polypeptide of SEQ ID NO: 9, wherein the variant has polyhydroxyalkanoate polymerase activity and comprises the amino acid sequence of SEQ ID NO: 10.

8. A variant of the polypeptide of SEQ ID NO: 9, wherein the variant has polyhydroxyalkanoate polymerase activity and comprises the amino acid sequence of SEQ ID NO: 10.

9. A method for preparing viscous polyhydroxyalkanoate that comprises:

(i) inoculating a fermentation culture medium with the genetically engineered bacterium according to claim 4, and performing a fermentation;

(ii) harvesting biomass from the fermentation; and (iii) extracting the viscous polyhydroxyalkanoate from the biomass;

wherein the fermentation culture medium comprises 10 g/L to 40 g/L glucose; 1 g/L to 3.5 g/L 10-undecenoic acid and lysogeny broth medium.

10. The method according to claim 9, wherein the fermentation is performed at a temperature of 28 ° C. to 42 ° C. for a time period of 12 hours to 72 hours with a rotation speed of 150 rpm to 300 rpm.

* * * * *

```
                          SEQUENCE LISTING

Sequence total quantity: 16
SEQ ID NO: 1            moltype = DNA  length = 29
FEATURE                 Location/Qualifiers
source                  1..29
                        mol_type = other DNA
                        organism = synthetic construct
SEQUENCE: 1
acacaggaca tcaatcgcgc tcacttcgt                                  29

SEQ ID NO: 2            moltype = DNA  length = 27
FEATURE                 Location/Qualifiers
source                  1..27
                        mol_type = other DNA
                        organism = synthetic construct
SEQUENCE: 2
ggacagtttg ctgttgccga tccagtc                                   27

SEQ ID NO: 3            moltype = DNA  length = 25
FEATURE                 Location/Qualifiers
source                  1..25
                        mol_type = other DNA
                        organism = synthetic construct
SEQUENCE: 3
gaacagcgtg agtggggtct gtcga                                     25

SEQ ID NO: 4            moltype = DNA  length = 23
FEATURE                 Location/Qualifiers
source                  1..23
                        mol_type = other DNA
                        organism = synthetic construct
SEQUENCE: 4
cttggtcggg ttgcgccagc tga                                       23

SEQ ID NO: 5            moltype = DNA  length = 28
FEATURE                 Location/Qualifiers
source                  1..28
                        mol_type = other DNA
                        organism = synthetic construct
SEQUENCE: 5
agcgacatgg ccaaagtctt cgcctgga                                  28

SEQ ID NO: 6            moltype = DNA  length = 24
FEATURE                 Location/Qualifiers
source                  1..24
                        mol_type = other DNA
                        organism = synthetic construct
SEQUENCE: 6
gccttccagc acgccggcct gata                                      24

SEQ ID NO: 7            moltype = DNA  length = 32
FEATURE                 Location/Qualifiers
source                  1..32
                        mol_type = other DNA
                        organism = synthetic construct
SEQUENCE: 7
cagtcttgct acaagtcggc gcaactgttc gg                             32

SEQ ID NO: 8            moltype = DNA  length = 27
FEATURE                 Location/Qualifiers
source                  1..27
                        mol_type = other DNA
                        organism = synthetic construct
SEQUENCE: 8
ccagggcgtg atgtgatcgt tggtgcc                                   27

SEQ ID NO: 9            moltype = AA  length = 559
FEATURE                 Location/Qualifiers
source                  1..559
                        mol_type = protein
                        organism = synthetic construct
SEQUENCE: 9
MSNKNSDDLN RQASENTLGL NPVIGLRGKD LLTSARMVLT QAIKQPIHSV KHVAHFGIEL  60
```

```
KNVMFGKSKL QPESDDRRFN DPAWSQNPLY KRYLQTYLAW RKELHDWIGN SKLSEQDINR     120
AHFVITLMTE AMAPTNSAAN PAAVKRFFET GGKSLLDGLT HLAKDLVNNG GMPSQVDMGA     180
FEVGKSLGTT EGAVVFRNDV LELIQYRPTT EQVHERPLLV VPPQINKFYV FDLSPDKSLA     240
RFCLSNNQQT FIVSWRNPTK AQREWGLSTY IDALKEAVDV VSAITGSKDI NMLGACSGGI     300
TCTALLGHYA ALGEKKVNAL TLLVTVLDTT LDSQVALFVD EKTLEAAKRH SYQAGVLEGR     360
DMAKVFAWMR PNDLIWNYWV NNYLLGNEPP VFDILFWNND TTRLPAAFHG DLIEMFKNNP     420
LVRANALEVS GTPIDLKQVT ADIYSLAGTN DHITPWKSCY KSAQLFGGKV EFVLSSSGHI     480
KSILNPPGNP KSRYMTSTDM PATANEWQEN STKHTDSWWL HWQAWQAERS GKLKKSPTSL     540
GNKAYPSGEA APGTYVHER                                                 559

SEQ ID NO: 10             moltype = AA   length = 559
FEATURE                   Location/Qualifiers
source                    1..559
                          mol_type = protein
                          organism = synthetic construct
SEQUENCE: 10
MSNKNSDDLN RQASENTLGL NPVIGLRGKD LLTSARMVLT QAIKQPIHSV KHVAHFGIEL     60
KNVMFGKSKL QPESDDRRFN DPAWSQNPLY KRYLQTYLAW RKELHDWIGN SKLSTQDINR     120
AHFVITLMTE AMAPTNSAAN PAAVKRFFET GGKSLLDGLT HLAKDLVNNG GMPSQVDMGA     180
FEVGKSLGTT EGAVVFRNDV LELIQYRPTT EQVHERPLLV VPPQINKFYV FDLSPDKSLA     240
RFCLSNNQQT FIVSWRNPTK EQREWGLSTY IDALKEAVDV VSAITGSKDI NMLGACSGGI     300
TCTALLGHYA ALGEKKVNAL TLLVTVLDTT LDSQVALFVD EKTLEAAKRH SYQAGVLEGS     360
DMAKVFAWMR PNDLIWNYWV NNYLLGNEPP VFDILFWNND TTRLPAAFHG DLIEMFKNNP     420
LVRANALEVS GTPIDLKQVT ADIYSLAGTN DHITPWQSCY KSAQLFGGKV EFVLSSSGHI     480
KSILNPPGNP KSRYMTSTDM PATANEWQEN STKHTDSWWL HWQAWQAERS GKLKKSPTSL     540
GNKAYPSGEA APGTYVHER                                                 559

SEQ ID NO: 11             moltype = AA   length = 559
FEATURE                   Location/Qualifiers
source                    1..559
                          mol_type = protein
                          organism = Pseudomonas sp.
SEQUENCE: 11
MSNKNSDDLN RQASENTLGL NPVIGLRGKD LLTSARMVLT QAIKQPIHSV KHVAHFGIEL     60
KNVMFGKSKL QPESDDRRFN DPAWSQNPLY KRYLQTYLAW RKELHDWIGN SKLSEQDINR     120
AHFVITLMTE AMAPTNSAAN PAAVKRFFET GGKSLLDGLT HLAKDLVNNG GMPSQVDMGA     180
FEVGKSLGTT EGAVVFRNDV LELIQYRPTT EQVHERPLLV VPPQINKFYV FDLSPDKSLA     240
RFCLSNNQQT FIVSWRNPTK AQREWGLSTY IDALKEAVDV VSAITGSKDI NMLGACSGGI     300
TCTALLGHYA ALGEKKVNAL TLLVSVLDTT LDSQVALFVD EKTLEAAKRH SYQAGVLEGR     360
DMAKVFAWMR PNDLIWNYWV NNYLLGNEPP VFDILFWNND TTRLPAAFHG DLIEMFKNNP     420
LVRANALEVS GTPIDLKQVT ADIYSLAGTN DHITPWKSCY KSAQLFGGKV EFVLSSSGHI     480
QSILNPPGNP KSRYMTSTDM PATANEWQEN STKHTDSWWL HWQAWQAERS GKLKKSPTSL     540
GNKAYPSGEA APGTYVHER                                                 559

SEQ ID NO: 12             moltype = AA   length = 559
FEATURE                   Location/Qualifiers
source                    1..559
                          mol_type = protein
                          organism = Pseudomonas sp.
SEQUENCE: 12
MSNKNNDDLK RQASENTLGL NPVIGLRKKD LLTSARMVLT QAIKQPLHSV KHVAHFGVEL     60
KNVMFGKSTL APESDDRRFN DPAWSQNPLY KRYMQTYLAW RKELHDWIGD SSLSEQDISR     120
AHFVINLMTE AMAPTNSAAN PAAVKRFFET GGKSLLDGLS HLAKDLVHNG GMPSQVNMGA     180
FEVGKSLGTT EGSVVFRNDV LELIQYRPIT EQVHERPLLV VPPQINKFYV FDLSPDKSLA     240
RFCLRSNVQT FIVSWRNPTK AQREWGLSTY IDALKEAVDV VTAITGSKDV NMLGACSGGI     300
TCTALLGHYA ALGEKKVNAL TLLVSVLDTT LDTQVALFVD EQTLEAAKRH SYQAGVLEGS     360
DMAKVFAWMR PNDLIWNYWV NNYLLGNEPP VFDILFWNND TTRLPAAFHG DLIEMFKNNP     420
LVRANALEVC GTPIDLKQVT ADVYSLAGTN DHITPWKSCY KSAQLFGGKV EFVLSSSGHI     480
QSILNPPGNP KSRYMTSTDM PADANAWQEN SSKHTDSWWL HWQAWQAERS GKLKKAPTSL     540
GSKTYPAAEA APGTYVHER                                                 559

SEQ ID NO: 13             moltype = AA   length = 559
FEATURE                   Location/Qualifiers
source                    1..559
                          mol_type = protein
                          organism = Pseudomonas sp.
SEQUENCE: 13
MSNKNNDDLK RQASENTLGL NPVIGLRRKD LLTSARMVLT QAIKQPIHSV KHVAHFGIEL     60
KNVMLGKSEL QPEGDDRRFN DPAWSQNPLY RRYLQTYLAW RKELHDWIGE SSLSTQDISR     120
AHFVINLMTE AMAPTNSAAN PAAVKRFFET GGKSLLDGLS HLAKDLVHNG GMPSQVNMGA     180
FEVGKSLGTT EGAVVFRNDV LELIQYRPIT EQVHERPLLV VPPQINKFYV FDLSPDKSLA     240
RFCLRNNVQT FIVSWRNPTK AQREWGLSTY IEALKEAVDV VTAITGSKDV NMLGACSGGI     300
TCTALLGHYA ALGEKKVNAL TLLVSVLDTT LDSQVALFVD EQTLEAAKRH SYQAGVLEGR     360
DMAKVFAWMR PNDLIWNYWV NNYLLGNEPP VFDILFWNND TTRLPAAFHG DLIELFKNNP     420
LVRADALEVC GTPIDLKQVT ADVYSLAGTN DHITPWKSCY KSAQLFGGKV EFVLSSSGHI     480
QSILNPPGNP KSRYMTSTDM PVHANDWLEN STKHTDSWWL HWQAWQAERS GKLKKAPTVL     540
GNKTYAAGEA SPGTYVHER                                                 559

SEQ ID NO: 14             moltype = AA   length = 559
```

```
FEATURE              Location/Qualifiers
source               1..559
                     mol_type = protein
                     organism = Pseudomonas sp.
SEQUENCE: 14
MSNKNNDDLK RQASENTLGL NPVIGLRRKD LLTSARMVLT QAIRQPLHSA KHVAHFGVEL   60
KNVMFGKSTL QPESDDRRFN DPAWSQNPLY KRYLQTYLAW RKELHDWIGQ SNLSEQDISR  120
GHFVINLMTE AMAPTNTAAN PAAVKRFFET GGKSLLDGLS HLAKDLVHNG GMPSQVNMDA  180
FEIGKNLGTS EGAVVFRNDV LELIQYRPVT EQVHERPLLV VPPQINKFYV FDLSPDKSLA  240
RFCLRNGLQT FIVSWRNPTK AQREWGLSTY IEALKEAVDV VTAITGSKDV NMLGACSGGI  300
TCTALLGHYA ALGEKKVNAL TLLVSVLDTT LDTQVALFVD EQTLEAAKRH SYQAGVLEGR  360
DMAKVFAWMR PNDLIWNYWV NNYLLGNEPP VFDILFWNND TTRLPAAFHG DLIEMFKNNP  420
LIRPNALEVC GTPIDLKQVT ADIFSLAGTN DHITPWKSCY KSAQLFGGKV EFVLSSSGHI  480
QSILNPPGNP KSRYMTSEEM PASADLWQEN STKHTDSWWL HWQAWQAERS GKLKKTPSIL  540
GNKAYPAAEA APGTYVHER                                               559

SEQ ID NO: 15          moltype = AA   length = 559
FEATURE              Location/Qualifiers
source               1..559
                     mol_type = protein
                     organism = Pseudomonas sp.
SEQUENCE: 15
MSNKNNDDLK RQASENTLGL NPVIGLRRKD LLTSARMVLT QAIKQPLHSA KHVAHFGVEL   60
KNVIFGKSTL QPESDDRRFN DPAWSQNPLY KRYLQTYLAW RKELHDWIGH SNLSEQDISR  120
GHFVINLMTE AMAPTNTAAN PAAVKRFFET GGKSLLDGLS HLAKDLVHNG GMPSQVNMDA  180
FEIGKNLGTS EGAVVFRNDV LELIQYRPVT EQVHERPLLV VPPQINKFYV FDLSPDKSLA  240
RFCLRNGLQT FIVSWRNPTK EQREWGLSTY IEALKEAVDV VTAITGSKDV NMLGACSGGI  300
TCTALLGHYA ALGEKKVNAL TLLVSVLDTT LDTQVALFVD EQTLEAAKRH SYQAGVLEGR  360
DMAKVFAWMR PNDLIWNYWV NNYLLGNEPP VFDILFWNND TTRLPAAFHG DLIEMFKNNP  420
LIRPNALEVC GTPIDLKQVT ADIFSLAGTN DHITPWKSCY KSAQLFGGKV EFVLSSSGHI  480
QSILNPPGNP KSRYMTSDEM PPSADDWQEN STKHTDSWWL HWQAWQAERS GKLKKTPSIL  540
GNKAYPAAEA APGTYVHER                                               559

SEQ ID NO: 16          moltype = AA   length = 559
FEATURE              Location/Qualifiers
source               1..559
                     mol_type = protein
                     organism = Pseudomonas sp.
SEQUENCE: 16
MSNKNNDDLK RQASENTLGL NPIIALRKKD LLASAKMVLT QAIKQPLHSV KHVAHFGVEL   60
KNVMFGKSQL VPESDDRRFH DPAWSQNPLY KRYLQTYLAW RKELHDWIGD SNLSEQDISR  120
GHFVINLMTE AMAPTNSAAN PAAVKRFFET GGKSLLDGLS HLAKDMVHNG GMPSQVNMGA  180
FEVGKSLGTT EGAVVFRNDV LELIQYKPIT EQVHERPLLV VPPQINKFYV FDLSPEKSLA  240
RFCLRNNQQT FIVSWRNPTK AQREWGLSTY IEALKEAVDV VTAITGSKDI NMLGACSGGI  300
TCTALLGHYA ALGEKKVNAL TLLVSVLDTT LDTQVALFVD EQTLEAAKRH SYQAGVLEGR  360
DMAKVFAWMR PNDLIWNYWV NNYLLGNEPP VFDILFWNND TTRLPAAFHG DLIELFKNNP  420
LVRANALEVC GTPIDLKQIT ADIYSLAGTN DHITPWQSCY KSAQLFGGKV EFVLSSSGHI  480
QSILNPPGNP KARYQTSDSL TAKPLEWQEN ATKHTDSWWL HWQAWQAERA GKLKKAPVSL  540
GNKTYAAGEA APGTYVHER                                               559
```